United States Patent
Hunter et al.

(10) Patent No.: US 7,648,735 B2
(45) Date of Patent: Jan. 19, 2010

(54) OXIDIZED ZIRCONIUM ON A POROUS STRUCTURE FOR BONE IMPLANT USE

(75) Inventors: Gordon Hunter, Memphis, TN (US); Vivek Pawar, Memphis, TN (US)

(73) Assignee: Smith & Nephew, Inc., Memphis, TX (US)

( * ) Notice: Subject to any disclaimer, the term of this patent is extended or adjusted under 35 U.S.C. 154(b) by 482 days.

(21) Appl. No.: 11/198,446

(22) Filed: Aug. 5, 2005

(65) Prior Publication Data

US 2006/0020346 A1   Jan. 26, 2006

Related U.S. Application Data

(62) Division of application No. 10/737,568, filed on Dec. 16, 2003, now Pat. No. 6,974,625.

(51) Int. Cl.
    *C23C 16/00* (2006.01)
(52) U.S. Cl. ............... 427/248.1; 623/22.15; 623/23.5; 623/23.53; 623/23.55; 623/23.71; 623/23.34; 623/23.51; 623/18.11; 623/20.14; 623/22.17; 623/22.24; 623/16; 623/11; 623/66; 623/22; 623/22.21; 501/1; 427/2; 427/2.24; 427/2.26; 427/2.27; 427/255.1; 427/255.12; 427/255.19; 419/2
(58) Field of Classification Search ............ 623/16, 623/22.15, 23.5, 18.11, 20.14, 22, 23.34, 623/23.51, 22.21; 419/2; 427/248.1
See application file for complete search history.

(56) References Cited

U.S. PATENT DOCUMENTS

| | | | |
|---|---|---|---|
| 5,169,597 A | 12/1992 | Davidson et al. | |
| 5,211,663 A | 5/1993 | Kovacs et al. | |
| 5,282,861 A * | 2/1994 | Kaplan | 623/23.51 |
| 5,372,660 A | 12/1994 | Davidson et al. | |
| 5,415,704 A | 5/1995 | Davidson | |
| 6,063,442 A | 5/2000 | Cohen et al. | |
| 6,087,553 A | 7/2000 | Cohen et al. | |
| 6,447,550 B1 * | 9/2002 | Hunter et al. | 623/22.15 |
| 2002/0042656 A1 | 4/2002 | Hunter et al. | |
| 2003/0044301 A1* | 3/2003 | Lefebvre et al. | 419/2 |
| 2003/0125808 A1 | 7/2003 | Hunter et al. | |
| 2003/0153979 A1 | 8/2003 | Hughes et al. | |
| 2003/0153981 A1 | 8/2003 | Wang et al. | |
| 2004/0122524 A1 | 6/2004 | Hunter et al. | |
| 2006/0052880 A1 | 3/2006 | Brosnahan et al. | |
| 2007/0137734 A1 | 6/2007 | Pawar et al. | |

OTHER PUBLICATIONS

Gambogi, Zirconium and Hafnium, [no month available] 1993, Ecology and Natural Resources: Minerals yearbook 1993, as supplied pp. 1-5.*

(Continued)

*Primary Examiner*—Michael Barr
*Assistant Examiner*—Andrew Bowman
(74) *Attorney, Agent, or Firm*—Fulbright & Jaworski, L.L.P.

(57) ABSTRACT

A composition, a medical implant constructed from the composition, and a method of making the composition are described. The composition is a composite material, comprising a porous, reticulated, open cell network having at least part of its surface coated with blue-black or black oxidized zirconium.

14 Claims, 1 Drawing Sheet

OTHER PUBLICATIONS

Gambogi, Zirconium and Halfnium, 1993, Ecology and Minerals Resources: Minerals Yearbook,, pp. 1-5.*

Fang et al., Characterization of HfO2 depsoited by photo-induced chemical vapour deposition, Mar. 2003, Thin Solid Films, vol. 427, pp. 391-396.*

Tuffias, Robert "Novel Material Spinal Implants," BMDO Technologies for biomedical Applications Chapter 3 Intervention Technologies Section A-Implants.

* cited by examiner

OXIDIZED ZIRCONIUM ON A POROUS STRUCTURE FOR BONE IMPLANT USE

This application is a divisional application of, and claims priority to, U.S. application Ser. No. 10/737,568, filed on Dec. 16, 2003 now U.S. Pat. No. 6,974,625.

TECHNICAL FIELD

This invention relates to composite materials having an open cell structure onto which one or more other materials are deposited. The composite material is particularly applicable to bone-implant uses, but may also be used in other applications.

BACKGROUND OF THE INVENTION

There is an ongoing need for replacement materials for cancellous bone, particularly where such materials are cell and tissue receptive. It is desirable that cancellous bone replacement materials provide a porous framework allowing for revascularization as well as new bone growth, and one which provides a compatible site for osteoprogenitor cells and bone growth-inducing factors. Grafting, however, requires surgery to obtain natural material, and a viable substitute synthetic material is desirable. Thus, a suitable, synthetic cancellous bone replacement material would be beneficial to these ends. In order to mimic the behavior of cancellous bone grafts, it is expected that the physical characteristics of this material should be reproduced in the synthetic material. Thus, any such material should be strong, biocompatible, should match the biomechanical requirements and performance of the natural material and have a porous framework which promotes revascularization and bone regrowth. For these latter two processes to occur, it is critical that bone ingrowth into and onto the replacement material occur to an appreciable extent.

The voids and interstices of a porous material provides surfaces for bone ingrowth, thereby providing ideal skeletal fixation for the permanent implants used for the replacement of bone segments lost due to any number of reasons, or in total joint prostheses. The implants may be conventional total joint replacements such as artificial hip, knees, etc., or partial joint replacements such endoprostheses components. A number of characteristics are known in the art to be important. These include porosity, biological compatibility, intimate contact with the surrounding bone, and adequate early stability allowing for bone ingrowth. The ideal porous replacement material should have good strength, especially good crack and impact resistance and a compliance comparable to that of bone. The material should be ideally be amenable to the easy and simple manufacture of implants of precise dimensions, and permit the fabrication of either thick or thin coatings on the materials.

One important requirement for successful ingrowth is that the implant material be placed next to healthy bone. In fact, the presence of bone within the implant demonstrates the osteoconductive, or bone-growth promoting properties of the porous structure of the implant when it is placed in physical contact with healthy bone tissue. Initially, the cells that interface the implant convert to bone, then the front of regenerated bone progresses into the implant.

There have been numerous efforts to develop and manufacture synthetic porous implants having the proper physical properties required to promote bone ingrowth. Implants with porous surfaces of metallic, ceramic, polymeric, or composite materials have been studied extensively over the last two decades.

The most commonly used substance for porous biomaterials is calcium hydroxyapatite (HA), which is the largest chemical constituent of bone. Other nonmetallic materials frequently used in porous form for implants include the ceramics tricalcium phosphate (TCP), calcium aluminate, and alumina, carbon; various polymers, including polypropylene, polyethylene, and polyoxymethylene (delrin); and ceramic-reinforced or-coated polymers. Unfortunately, ceramics, while strong, are very brittle and often fracture readily under loading; and polymers, while possessing good ductility, are extremely weak. The very nature of these materials can restrict their clinical dental and orthopedic applications.

Metals, on the other hand, combine high strength and good ductility, making them attractive candidate materials for implants (and effectively the most suitable for load-bearing applications). Many dental and orthopedic implants contain metal, most often titanium or various alloys such as stainless steel or vitallium (cobalt-chromium-molybdenum). Ceramic-coated metals are also used, typically HA or TCP on titanium. Additionally, a large variety of metals are used internally in biomedical components such as wire, tubing, and radiopaque markers.

Many existing metallic biomaterials, however, do not easily lend themselves to fabrication into the porous structures that are most desirable for bone implants. These materials (e.g. stainless steel, cobalt-based alloys) exhibit the necessary properties and biocompatibility as long as only a smooth, bulk shape in a metallurgically perfect state is needed. The machining or other treatment needed to obtain a porous or surface-textured shape for interlocking with skeletal tissue can have a detrimental effect on the properties and biocompatibility, and can even result in material failure. For example, the hexagonal crystal structure of titanium makes it susceptible to cracks and fractures, as has been seen in the case of dental implants. Some porous metallic materials (e.g. flame- or plasma-sprayed titanium, porous sintered powder metallurgy materials) do not match the structure of cancellous bone sufficiently well to ensure successful ingrowth and integration. Also, most metals and alloys currently in use are subject to some degree of corrosion in a biological environment. Finally, the high densities of metals can make them undesirable from a weight standpoint.

A significant step in the improvement of porous implants occurred with the introduction of a reticulated open cell carbon foam is infiltrated with tantalum by the chemical vapor deposition (CVD) process that was described in U.S. Pat. No. 5,282,861. The '861 patent taught a new biomaterial that, when placed next to bone or tissue, initially serves as a prosthesis and then functions as a scaffold for regeneration of normal tissues. The '861 material fulfills the need for an implant modality that has a precisely controllable shape and at the same time provides an optimal matrix for cell and bone ingrowth. The physical and mechanical properties of the porous metal structure can be specifically tailored to the particular application at hand. Although it is expected to have its greatest application in orthopedics, this new implant material offers the potential for use in alveolar ridge augmentation, periodontics, and other applications. As an effective substitute for autografts, it will reduce the need for surgery to obtain those grafts.

The open cell structure of the prior art is made from tantalum. Most of the current orthopaedic implants are made from titanium or cobalt chromium alloy, or more recently from zirconium alloy. The use of tantalum along with the titanium or cobalt chromium alloy poses a possibility of galvanic interaction, the effects of which are currently not known. A porous structure that is made from an alloy which is currently used in the orthopaedic industry will be a great advantage as it can be safely incorporated with the existing alloying system. However, the open cell structures of the prior art suffered from a lack of strength for certain implant applications. An improvement in the state of the art of porous implant structures may be achieved if the strength of the structure can be improved. This would facilitate its widespread use in both conventional implants such as hip, knees, etc., as well as in specialty applications such as replacements for vertebral bodies that make up the spinal column.

BRIEF SUMMARY OF THE INVENTION

The present invention is directed to a composition, a medical implant constructed from the composition, and a method of making the composition. The composition is a composite material, comprising a porous, reticulated, open cell network having at least part of its surface coated with blue-black or black oxidized zirconium. The substrate material comprising the open cell network may comprise any material having suitable strength for a given application. Non-limiting examples include metal, carbon foam, or polymer material.

In one aspect of the present invention there is a composite material comprising a reticulated open cell substrate formed of a substantially rigid foam material, said substrate comprising an interconnecting network having interconnected continuous channels, and a surface layer of blue-black or black oxidized zirconium.

In one embodiment of the composite material, the surface layer substantially covers said interconnecting network. In another embodiment of the composite material the foam material is carbonaceous material. In yet another embodiment of the composite material, the carbonaceous material is graphite. In another embodiment of the composite material, the foam material is a polymer material. In one embodiment, the polymer material comprises polyethylene. In another embodiment, the polymer material comprises polypropylene. In another embodiment, the polymer material comprises both polypropylene and polyethylene. In another embodiment of the composite material, the foam material is selected from the group consisting of ceramic, metal, and metal alloy. In another embodiment of the composite material, the material further comprises a second substrate material, the second substrate material being bonded to said open cell substrate.

In another aspect of the present invention there is a method of making a composite material comprising the steps of providing a material having a reticulated open cell structure, depositing a layer of zirconium or zirconium alloy onto said substrate; and, oxidizing said layer to blue-black or black oxidized zirconium.

In one embodiment of the method, the step of depositing comprises chemical vapor deposition or physical vapor deposition or both. In another embodiment of the method, the step of oxidizing comprises oxidizing using air, steam, or water oxidation or any combination thereof. In yet another embodiment of the method, the step of oxidizing comprises oxidizing in a furnace having an oxygen-containing atmosphere.

In another aspect of the present invention there is a method of making a composite material comprising the steps of providing a material having a reticulated open cell structure, physically constructing a layer of zirconium or zirconium alloy onto said substrate, and oxidizing said layer to blue-black or black oxidized zirconium.

In one embodiment of the method, the step of physical construction comprises direct casting. In another embodiment of the method, the step of physical construction comprises building a diffusion-bonded layer.

In another aspect of the present invention there is a medical implant comprising a composite material, said composite material comprising a reticulated open cell substrate formed of a substantially rigid foam material said substrate comprising an interconnecting network having interconnected continuous channels, and a surface layer of blue-black or black oxidized zirconium.

In a specific embodiment of the medical implant, the medical implant is a hip prosthesis. In another embodiment, the medical implant is a knee prosthesis. In another embodiment, the medical implant is a spinal prosthesis. In yet another embodiment, the medical implant is a spinal prosthesis and the spinal implant is a vertebral body. In another embodiment, the medical implant is a bone graft.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying FIGURE. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

Figure 1:
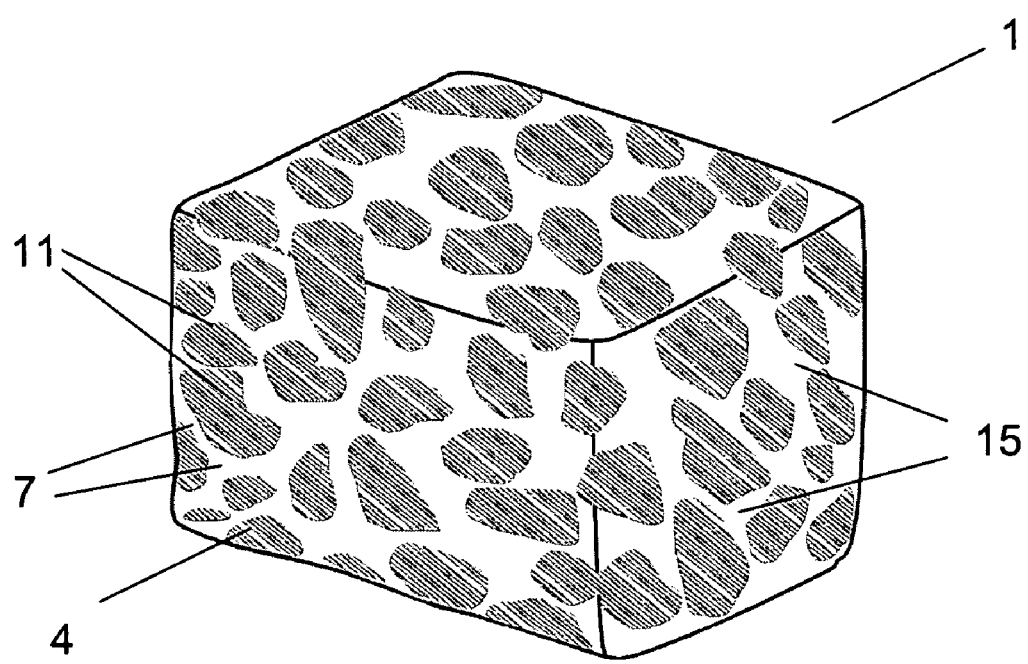
FIG. 1 is a schematic illustration of an open cell structure of the present invention.

As used herein, "a" and "an" include both the singular and the plural and mean one or more than one.

New materials are enabling the design of innovative, and increasingly biocompatible, replacements for damaged human tissues. In the present invention, reticulated open cell carbon foam is infiltrated with zirconium or zirconium alloy by any of a number of techniques known in the art, including any deposition-based techniques known in the art such as, for example, chemical vapor deposition (CVD), physical vapor deposition (PVD), and arc deposition. The zirconium or zirconium alloy is then oxidized to a blue-black or black oxidized zirconium, which has the optimum combinations of the beneficial properties of ceramics and metals while suffering little, if at all, from the disadvantages of either. Additionally, physical construction of the composition is another possible route and such techniques include, for example, direct casting or building a diffusion-bonded layer.

The porous substrate material may be any material having a porous, open-cell network. Carbon foam, such as that disclosed in U.S. Pat. No. 5,282,861, hereby incorporated by reference as though full disclosed herein, is one example. Other possible substrate materials include polymeric materials, metallic materials including metal alloys, and ceramic materials. The only requirement of the substrate is that it possess an open-cell porous network and have sufficient strength as to impart appropriate structural integrity to the resulting composition. It preserves the structural strength of conventional implants, yet it is lightweight relative to the same conventional implants. These porous substrates may be fabricated by any suitable techniques. Some examples include, but are not limited to, (i) polymer foams that are fabricated by introducing gas bubbles into the liquid monomer or hot polymer and formed into a reticulated network, (ii) metal foams that are fabricated by a powder metallurgy route and may or may not include selective leaching of one or more components, (iii) metal or ceramic foams that are fabricated by coating an open-cell polymer foam substrate using vapor deposition processes (chemical or physical) or electrochemical deposition processes, and (iv) metal or ceramic foams that are produced by plasma or flame spray deposition on polymer foams.

FIG. 1 is a schematic illustration of an open cell structure (1) of the present invention with deposited oxidized zirconium or zirconium alloy. Open spaces (4) are interconnected by structural material (7). The structure thus comprises interior surface (11) (the surfaces of the internal cells and interconnecting channels) and exterior surface (15) (the outward-facing surfaces). In the embodiment illustrated in FIG. 1, the surfaces of the open cells comprise blue-black or black oxidized zirconium (designated by cross-hatched regions (4) and (11)). As discussed below, other embodiments are within the scope of the invention, such as the embodiment wherein all surfaces (both the exterior surfaces as well as those of the open cells) comprise blue-black or black oxidized zirconium. While initial contact with surrounding bone or tissue would primarily occur through the exterior surface of the structure, bone and tissue ingrowth and on-growth would result in physical contact between the interior surface and surrounding bone and tissue also. With the variables available in both the materials and the fabrication process, it is possible to obtain the simultaneous optimization of multiple properties (e.g. strength, stiffness, density, weight) for the given application of substitution for bone.

A major advantage of the open cell structure described herein is that it is readily shapeable to nearly any configuration, simple or complex, simply by shaping the substrate material prior to application of the surface material. This facilitates exact contouring of the implant for the specific application and location; precise placement is enhanced and bulk displacement is prevented. Additionally, it appears that any final shaping/trimming needed at surgery can be accomplished on the final device using conventional dental or orthopedic equipment available at the time of surgery.

The optimal conditions for fracture healing and long-term stability can be met if an implant can be designed allowing for motionlessness along all the interfaces necessary for a stable anchorage, thereby excluding (to the greatest extent possible) all outside influences on the remodeling process and allowing the local stress/strain field to control.

Following implantation and initial tissue ingrowth, the foam device stays where it is placed without retention aids, a reflection of precise contouring and the rapid ingrowth of fibrovascular tissue to prevent dislodgement. The binding between bone and implant stabilizes the implant and prevents loosening. These implants thus will not need to be held in place by other means (e.g. sutures or cement); rather, the growth of a natural bone-to-bone seal is encouraged by the nature of the implant itself. Tissue ingrowth would not be a contributing factor to device retention for a period following implantation, however, until a substantial amount of ingrowth had occurred In one embodiment, a carbon foam substrate is infiltrated by chemical vapor deposition (CVD). The resulting lightweight, strong, porous structure, mimicking the microstructure of natural cancellous bone, acts as a matrix for the incorporation of bone or reception of cells and tissue. The pores of the matrix are connected to one another to form continuous, uniform channels with no dead ends. This intricate network of interconnected pores provides optimal permeability and a high surface area to encourage cell and tissue ingrowth, vascularization, and deposition of new bone.

The composite material may also be formed by physical vapor deposition. Alternatively, physical construction of the composition is another possible preparatory route and such techniques include, for example, direct casting or building a diffusion-bonded layer. These and other methods, which are known to those of skill in the art, are also part of the present invention.

The resulting composition is an exceptional biomaterial that, when placed next to bone or tissue, initially serves as a prosthesis and then functions as a scaffold for regeneration of normal tissues. It satisfies the need for an implant modality that has a precisely controllable shape and at the same time provides an optimal matrix for cell and bone ingrowth. Additionally, the physical and mechanical properties of the porous metal structure can be specifically tailored to the particular application at hand. This new implant offers the potential for use in alveolar ridge augmentation, periodontics, and orthognathic reconstruction. As an effective substitute for autografts, it will reduce the need for surgery to obtain those grafts. It is useful in orthopedic applications as well.

The present invention may also be used for tooth replacement because of the ability to induce tissue and bone growth even in the face of mildly infectious conditions. For example, an artificial tooth can be joined to an open cell tantalum stem and positioned in an appropriately sized hole in the jaw. The gum is allowed to rest against the artificial tooth and some of the stem to form a seal.

Oxidized zirconium is chosen as the surface material due to its high strength and high wear resistance. The oxidized zirconium surface of the composition of the subject invention is also useful in providing a biocompatible, inert ceramic barrier between the substrate and any body fluids which may otherwise come into contact with the substrate material. Thus, since the oxidized zirconium surface is not prone to ionization and wear-induced corrosion, both the life span and the biocompatibility of the implant composition are enhanced.

Additionally, the natural in situ formation of an oxidized zirconium surface from the presence of zirconium in the substrate metal involves oxygen diffusion into the substrate below the oxide coating. This is helpful when the substrate comprises metal or metal alloy. Oxygen, an alloying constituent in zirconium, increases the strength of the metal substrate, particularly the fatigue strength. Resistance to fatigue loading is paramount in many implant applications. Thus, not only does the formation of the oxidized zirconium surface improve wear, friction, and corrosion resistance, it also improves the mechanical integrity of the implant device from a strength standpoint.

Cancellous, or spongy, bone is composed of a porous space-frame structure formed of open spaces defined by interconnected trabeculae, oriented along lines of principal stresses. At the microstructural level, the trabeculae are composed of layers of lamellar bone. Cancellous bone has anisotropic mechanical properties, i.e. different structural behavior along different orientations. Along the axis of the major channels, cancellous bone exhibits elastic behavior with sudden brittle failure at ultimate load in tension. When loaded with a tensile force whose line of action is skewed with respect to the channel axis of the bone, the stress-strain curve is parabolic with plastic deformation and greater energy absorption. It is therefore stiffer (has higher tensile and compressive moduli) but fails at a lower strain when loaded parallel to the predominant spicular direction than when loaded in other directions. These properties are important because they serve to absorb shock and distribute load in the vicinity of the articular surfaces of joints.

Any material to be used as a substitute for cancellous bone must therefore allow elastic deformation and load distribution. In addition, the material must not produce load concentrations, particularly if placed close to the underlying surface of articular cartilage, which might increase the local stresses on the articular surface and lead to wear and damage of the surface.

Materials for osseous, or bone, implants must be rigid and stress-resistant, while avoiding self-concentration of stresses that result in stress shielding. Also, osseous implants should ideally reside in the bone without interfering with bone remineralization, the natural process by which the body replenishes bone. The implant should be able to be precisely shaped and placed for optimal interface and performance. Finally, non-resorption would be a beneficial quality for implants used in load-bearing applications, and/or those in which complete bone ingrowth is not possible.

Completeness of the interconnectivity of a porous implant helps to improve performance. This is so because constrictions between pores and isolated, deadend pockets can limit vascular support to ingrowing tissues; ischemia of the ingrowing bone cells results in failure of the implant. Incomplete vascularization or a reduction in the neovascularity also makes an implant increasingly vulnerable to bacterial colonization. Implants lacking completely interconnected porosity can also result in aberrant mineralization, stress shielding, low fatigue strength, and/or bulk displacement.

The open cell metal structure of the present invention offers highly interconnected, three-dimensional porosity that is uniform and consistent, a structure exceptionally similar to that of natural cancellous bone. In this way it is superior to other porous metallic implant materials, whose "porosity" is artificially produced via some form of surface treatment that does not result in a truly complete, open porosity. Examples of these methods include macroscopic porous coatings (e.g. metal microspheres or wires sintered or otherwise attached to a bulk surface); microscopic surface porosity (e.g. metal powder particles flame- or plasma-sprayed onto a bulk surface); and controlled surface undulations machined into a bulk surface.

Although certain porous ceramic materials do offer full porosity (e.g. the replamineform process for hydroxyapatite), they have properties inferior to metals as discussed previously. The open cell metal structure is osteoconductive, like other porous implants.

Allowing full mineralization is another extremely important property required of bone substitute materials. The highly organized process of bone formation is a complex process and is not fully understood. There are, however, certain prerequisites for mineralization such as adequate pore size, presumably larger than 150 μm with interconnect size in the range of 75 μm. A pore diameter of 200 μm corresponds to the average diameter of an osteon in human bone, while a pore diameter of 500 μm corresponds to remodeled cancellous bone. The open cell metal structures of the present invention can be fabricated to virtually any desired porosity and pore size, and can thus be matched perfectly with the surrounding natural bone in order to provide an optimal matrix for ingrowth and mineralization. Such close matching and flexibility are generally not available with other porous implant materials.

One concern with an implant must be the potential for stress shielding. According to Wolff's law, bone grows where it is needed (that is, where there is a stress). Stress on a bone normally stimulates that bone to grow. With an implant, it is primarily the stress/strain field created in the tissue around an implant that controls the interface remodeling. Stress shielding occurs when an overly stiff implant carries stresses that were previously applied to the bone in that area; it can result in inhibition of mineralization and maturation of the ingrowing bone, and/or the resorption of existing natural bone.

An implant, then, should ideally distribute stresses throughout its structure, the ingrowing bone, and the surrounding bone in order to avoid bone resorption and weakening caused by stress shielding. Because metals are stronger than natural bone, this would seem to be a concern with a metallic implant in that the implant would itself focus and bear directly the majority of local loads and stresses that would ordinarily be placed on the bone, thus depriving both the existing and new bone of those forces which, in effect, help keep it at optimal strength.

The unique structure and properties of the open cell metal structures of the present invention, however, avoid this drawback altogether. The deposited thin films operate as an array within the porous metal body, contributing their exceptional mechanical properties to the structure at large. One result of this effect is that imposed loads are distributed throughout the body. In the case of a open cell metal bone implant, stresses are distributed into both the ingrowing new bone and the surrounding existing bone as well, thereby providing both the old and new bone with the normal, healthy forces they require.

In fact, with the ability to finely tailor the open cell metal structure's properties during the fabrication process, an implant can be designed to distribute stresses in a given direction(s), depending on the needs of the specific application at hand. The bonding of regenerated bone to the implant also helps to transfer stresses directly to the bone in and around the implant; this sharing of biofunction is a consequence of the composite nature of the implant/bone structure. The advantage of these metal structures over other porous implant materials is especially strong in this area. Ceramics lack sufficient mechanical properties to begin with, and no current implant material, either ceramic or metallic, possesses the unique properties of the metal structure as described here.

In the present invention, useful refractory structures are preferably made by deposition techniques the chemical vapor deposition and physical vapor deposition of a small amount of zirconium or zirconium alloy into a reticulated (porous) vitreous structure. Preferably, this is carbon foam, but may be any other material having an open cell, porous network. The density of the resultant body is purposely maintained at substantially below full density, resulting in a structure with extremely favorable properties. On preferred embodiment involves the use of a low-density carbon foam, which is infiltrated with the desired material by CVD to provide uniform thin films on all ligaments. These thin films provide exceptional strength and stiffness to the ligaments, with the expenditure of very little weight. Thin CVD films can provide much higher mechanical properties than can bulk materials. Such quasi-honeycomb materials have remarkably high specific strength and stiffness.

This process does not endeavor to densify the body fully, although it is possible to do so, and useful parts can be so fabricated. In the present invention, thin films are located on the surfaces of the open cell, porous substrate, taking advantage of the apparent unusual mechanical properties of the thin films. Using a porous carbon with extremely high porosity and small pore size takes advantage not only of the properties of thin films, but of short beams as well.

It is permissible that the structural integrity of the fabricated structure is provided by the deposited thin films themselves, rather than by the open cell porous substrate. These films may have much higher moduli of elasticity than do the substrate materials. Because the deposited films are so thin and short, they show great strength, not unlike the high strength experienced in very fine fibers or filaments. Their support of the mechanical load ensures that failure does not occur in the substrate material.

The substrate material may be carbon foam, a polymer such a polyethylene or polypropylene. The material may also be metal or ceramic. The only requirement is that the substrate possess a reticulated, open cell, porous network.

The reticulated, open cell, porous network is infiltrated by zirconium metal or a zirconium alloy. The zirconium metal or zirconium alloy is then oxidized to blue-black or black oxidized zirconium. The resulting lightweight, strong, porous structure, mimicking the microstructure of natural cancellous bone, acts as a matrix for the incorporation of bone or reception of cells and tissue. The pores of the matrix are connected to one another to form continuous, uniform channels with no dead ends. This network of interconnected pores provides optimal permeability and a high surface area to encourage cell and tissue ingrowth, vascularization, and deposition of new bone.

The result is a novel biomaterial that, when placed next to bone or tissue, initially serves as a prosthesis and then functions as a scaffold for regeneration of normal tissues. The new biomaterial fulfills the need for an implant modality that has a precisely controllable shape and at the same time provides an optimal matrix for cell and bone ingrowth as well as having a high strength, inert surface. Additionally, the physical and mechanical properties of the porous structure can be specifically tailored to the particular application at hand. This new implant offers the potential for use in alveolar ridge augmentation, periodontics, and orthognathic reconstruction. As an effective substitute for autografts, it will reduce the need for surgery to obtain those grafts. It is useful in orthopedic applications as well.

Zirconium is used as the material of choice based on its good mechanical properties, excellent corrosion resistance, and demonstrated biocompatibility. Additionally, zirconium has superior properties upon is oxidation to a blue-black or black oxidized zirconium. Early evidence of excellent tissue acceptance, combined with low corrosion, has led to the use of oxidized zirconium as a specialty surgical implant material and its use in a variety of applications, resulting in superior conventional and unconventional prosthetic devices.

The zirconium or zirconium alloy is deposited onto the reticulated open cell substrate prior to oxidation. In order to form continuous and useful zirconium oxide coatings over the desired surface of the metal alloy prosthesis substrate, the zirconium alloy may have any amount of zirconium, but preferably should contain from about 80 to about 100 wt. % zirconium, and more preferably from about 95 to about 100 wt. %. However, alloys having lesser amounts of zirconium may be used. Oxygen, niobium, and titanium include common alloying elements in the alloy with often times the presence of hafnium. Yttrium may also be alloyed with the zirconium to enhance the formation of a tougher, yttria-stabilized zirconium oxide coating during the oxidation of the alloy. While such zirconium containing alloys may be custom formulated by conventional methods known in the art of metallurgy, a number of suitable alloys are commercially available. Non-limiting examples of such materials include those consisting of zirconium with 2.5% niobium (commercially known as Zircadyne 705), pure zirconium (commercially known as Zircadyne 702), and various other zirconium alloys have minor amounts of other components (such as the commercial product known as Zircalloy).

Any of various deposition methods well known in the art may be used to form a surface layer of zirconium or zirconium alloy. These include chemical vapor deposition (CVD), physical vapor deposition (PVD), or a combination thereof. A CVD process may include a gaseous or liquid precursor that contains zirconium. The precursors used may be an organometallic type or can be an inorganic compound. The precursor is decomposed to form metallic zirconium on the porous substrate. A PVD process may include evaporation of zirconium alloy in vacuum and subsequent condensation of these vapors on to the porous substrate. The evaporation may be carried out by heating the alloy (thus forming a melt) or by sputtering the alloy with inert gases or by arc discharge. An electrochemical deposition of zirconium alloy on to the porous substrates may also be accomplished by using fused salt electrolysis in which a zirconium salt is decomposed in order to deposit metallic zirconium onto the porous substrate.

In addition, other methods of fabrication are also possible. Physical construction of a porous structure of zirconium or zirconium alloy may be accomplished using direct casting methods known in the art. Alternatively, a cast porous structure may be coated with zirconium or zirconium alloy as described previously. Another approach for construction includes diffusion-bonding perforated metal layers (sheets or plates) to build an open-cell porous structure, with the metal layers composed of zirconium or zirconium alloy or with the metal layers subsequently coated with zirconium or zirconium alloy as described previously. Alternatively, the porous structure may be created by sintering metallic particles or beads of zirconium or zirconium alloy using methods known in the art, or sintering metallic particles or beads and subsequently coating them with zirconium or zirconium alloy as described previously.

Once deposited, the zirconium or zirconium alloy layer is oxidized to blue-black or black oxidized zirconium. The layer is then subjected to process conditions which cause the natural (in situ) formation of a tightly adhered, diffusion-bonded coating of zirconium oxide on its surface. The process conditions include, for instance, air, steam, or water oxidation or oxidation in a salt bath. These processes ideally provide a thin, hard, dense, blue-black or black, low-friction wear-resistant zirconium oxide film or coating of thicknesses typically on the order of several microns ($10^{-6}$ meters) on the surface of the prosthesis substrate. Below this coating, diffused oxygen from the oxidation process increases the hardness and strength of the underlying substrate metal.

The air, steam and water oxidation processes are described in now-expired U.S. Pat. No. 2,987,352 to Watson, the teachings of which are incorporated by reference as though fully set forth. Additional teachings are found in U.S. Pat. No. 5,037,438 to Davidson, the teachings of which are incorporated by reference as though fully set forth. The air oxidation process provides a firmly adherent black or blue-black layer of zirconium oxide of highly oriented monoclinic crystalline form. If the oxidation process is continued to excess, the coating will whiten and separate from the metal substrate. The oxidation step may be conducted in either air, steam or hot water. For convenience, the metal prosthesis substrate may be placed in a furnace having an oxygen-containing atmosphere (such as air) and typically heated at 700° F.-1100° F. up to about 6 hours. However, other combinations of temperature and time are possible. When higher temperatures are employed, the oxidation time should be reduced to avoid the formation of the white oxide.

It is preferred that a blue-black zirconium oxide layer ranging in thickness up to about 5 microns should be formed. However, larger thicknesses may be desired depending upon the particular application. For example, furnace air oxidation at 1000° F. for 3 hours will form an oxide coating on Zircadyne 705 about 4-5 microns thick. Longer oxidation times and higher oxidation temperatures will increase this thickness, but may compromise coating integrity. For example, one hour at 1300° F. will form an oxide coating about 14 microns in thickness, while 21 hours at 1000° F. will form an oxide coating thickness of about 9 microns. Of course, because only a thin oxide is necessary on the surface, only very small dimensional changes, typically less than 10 microns over the thickness of the prosthesis, will result. In general, thinner coatings (1-4 microns) have better attachment strength.

One of the salt-bath methods that may be used to apply the zirconium oxide coatings to the metal alloy prosthesis, is the method of U.S. Pat. No. 4,671,824 to Haygarth, the teachings of which are incorporated by reference as though fully set forth. The salt-bath method provides a similar, slightly more abrasion resistant blue-black or black zirconium oxide coating. The method requires the presence of an oxidation compound capable of oxidizing zirconium in a molten salt bath. The molten salts include chlorides, nitrates, cyanides, and the like. The oxidation compound, sodium carbonate, is present in small quantities, up to about 5 wt. %. The addition of sodium carbonate lowers the melting point of the salt. As in air oxidation, the rate of oxidation is proportional to the temperature of the molten salt bath and the '824 patent prefers the range 550° C.-800° C. (1022° C.-1470° C.). However, the lower oxygen levels in the bath produce thinner coatings than for furnace air oxidation at the same time and temperature. A salt bath treatment at 1290° F. for four hours produces an oxide coating thickness of roughly 7 microns.

Whether air oxidation in a furnace or salt bath oxidation is used, the zirconium oxide coatings are quite similar in hardness. For example, if the surface of a wrought Zircadyne 705 (Zr, 2-3 wt. % Nb) prosthesis substrate is oxidized, the hardness of the surface shows a dramatic increase over the 200 Knoop hardness of the original metal surface. The surface hardness of the blue-black zirconium oxide surface following oxidation by either the salt bath or air oxidation process is approximately 1700-2000 Knoop hardness.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method of making a composite material for medical implant use comprising the steps of:
   providing a medical implant material having a reticulated open cell structure,
   depositing a layer of zirconium or zirconium alloy onto said structure, wherein said zirconium or zirconium alloy has a zirconium content of from about 80 weight % to about 100 weight %; and,
   oxidizing said layer to blue-black or black oxidized zirconium.

2. The method of claim 1 wherein said step of depositing comprises chemical vapor deposition or physical vapor deposition or both.

3. The method of claim 1 wherein said step of oxidizing comprises oxidizing using air, steam, or water oxidation or any combination thereof.

4. The method of claim 1 wherein said step of oxidizing comprises oxidizing in a furnace having an oxygen-containing atmosphere.

5. The method of claim 1, wherein said step of depositing comprises electrochemical deposition.

6. The method of claim 2, wherein said step of depositing comprises chemical vapor deposition.

7. The method of claim 6, further comprising depositing a gaseous or liquid precursor containing zirconium.

8. The method of claim 7, wherein said precursor is an organometallic or an inorganic compound.

9. The method of claim 7, wherein said step of depositing comprises decomposing said precursor to form metallic zirconium on said substrate.

10. The method of claim 2, wherein said step of depositing comprises physical vapor deposition.

11. The method of claim 10, wherein said step of depositing comprises evaporation of zirconium alloy in vacuum and condensation of zirconium alloy vapors onto said substrate.

12. The method of claim 11, wherein said step of evaporation comprises heating the alloy, or sputtering the alloy with inert gases or arc discharge.

13. The method of claim 1, wherein said zirconium or zirconium alloy has a zirconium content of from about 95 weight % to about 100 weight %.

14. A method of making a composite material for medical implant use comprising the steps of:
   providing a medical implant material having a reticulated open cell structure,
   depositing by chemical vapor deposition a layer of zirconium or zirconium alloy onto said structure, wherein said zirconium or zirconium alloy has a zirconium content of from about 80 weight % to about 100 weight %; and,
   oxidizing said layer to blue-black or black oxidized zirconium by exposing said medical implant material having said deposited layer of zirconium or zirconium alloy to temperature of at least 700° F. in an oxygen-containing atmosphere.

* * * * *